(12) United States Patent
Chirik et al.

(10) Patent No.: US 12,180,149 B2
(45) Date of Patent: Dec. 31, 2024

(54) DEPOLYMERIZATION OF OLIGOMERS AND POLYMERS COMPRISING CYCLOBUTANE UNITS

(71) Applicant: The Trustees of Princeton University, Princeton, NJ (US)

(72) Inventors: Paul J. Chirik, Princeton, NJ (US); C. Rose Kennedy, Rochester, NY (US); Megan Mohadjer Beromi, Plainsboro, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 150 days.

(21) Appl. No.: 17/795,397

(22) PCT Filed: Jan. 28, 2021

(86) PCT No.: PCT/US2021/015403
§ 371 (c)(1),
(2) Date: Jul. 26, 2022

(87) PCT Pub. No.: WO2021/154931
PCT Pub. Date: Aug. 5, 2021

(65) Prior Publication Data
US 2023/0059241 A1 Feb. 23, 2023

Related U.S. Application Data

(60) Provisional application No. 62/966,863, filed on Jan. 28, 2020.

(51) Int. Cl.
*C07C 4/22* (2006.01)
*B01J 31/18* (2006.01)
*C07C 2/46* (2006.01)

(52) U.S. Cl.
CPC ............. *C07C 4/22* (2013.01); *B01J 31/1815* (2013.01); *C07C 2/46* (2013.01); *B01J 2531/842* (2013.01); *C07C 2531/18* (2013.01)

(58) Field of Classification Search
CPC ......... C07C 4/22; C07C 2/46; C07C 2531/18; C07C 2531/02; B01J 31/1815;
(Continued)

(56) References Cited

U.S. PATENT DOCUMENTS 5,369,215 A * 11/1994 Platz ................. C07C 4/22
264/912
6,482,908 B1  11/2002 Grubbs et al.
(Continued)

OTHER PUBLICATIONS

International Search Report and Written Opinion corresponding to PCT/US2021/015403, mailed Apr. 7, 2021, 5 pages.
(Continued)

*Primary Examiner* — Ali Z Fadhel
(74) *Attorney, Agent, or Firm* — J. Clinton Wimbish; Maynard Nexsen PC

(57) ABSTRACT

Methods of polymer and/or oligomer depolymerization are described herein which, in some embodiments, enable facile polymer and/or oligomer decomposition under mild, non-energy intensive conditions. Briefly, a method of depolymerization comprises providing a reaction mixture comprising a transition metal catalyst, and a polymer or oligomer having a backbone including cyclobutane units, and decomposing the polymer or oligomer to provide diene monomer or alkene monomer.

20 Claims, 8 Drawing Sheets

(58) Field of Classification Search
CPC .......... B01J 2531/842; B01J 2531/0244; B01J 2531/845; B01J 2531/847; C07F 15/02
See application file for complete search history.

(56) References Cited

U.S. PATENT DOCUMENTS

| | | |
|---|---|---|
| 9,409,850 B2 * | 8/2016 | Wagener .................. C07C 4/22 |
| 2013/0261198 A1 | 10/2013 | Alidedeoglu et al. |
| 2019/0211142 A1 | 7/2019 | Chirik et al. |

OTHER PUBLICATIONS

Beromi et al., "Iron-catalysed synthesis and chemical recycling of telechelic 1,3-enchained oligocyclobutanes", Nature Chemistry, Jan. 25, 2021 (Jan. 25, 2021), vol. 13, p. 156-162; entire document.

* cited by examiner

DEPOLYMERIZATION OF OLIGOMERS AND POLYMERS COMPRISING CYCLOBUTANE UNITS

RELATED APPLICATION DATA

This application is a U.S. National Phase of PCT/US2021/015403, filed Jan. 28, 2021, which claims priority pursuant to Article 8 of the Patent Cooperation Treaty to U.S. Provisional Patent Application Ser. No. 62/966,863, filed on Jan. 28, 2020, each of which is incorporated herein by reference in its entirety.

FIELD

The present application relates to oligomers and polymers comprising cyclobutane units and, in particular, to the depolymerization of such oligomers and polymers into diene monomeric units.

BACKGROUND

Plastic materials are an indispensable aspect of modern society. Plastic materials play critical roles in nearly every industry including food and drug processing and packaging, medical devices, and components for automobiles, aircraft, homes and buildings. Unfortunately, plastic waste proliferation poses a substantial threat to the sustainability or existence of natural environments. In view of this threat, plastic collection and recycling efforts are more important than ever. However, plastic recycling generally employs energy intensive, high temperature pyrolytic methods, which can induce further environmental damage via associated carbon release.

SUMMARY

In view of these disadvantages, methods of polymer and/or oligomer depolymerization are described herein which, in some embodiments, enable facile polymer and/or oligomer decomposition under mild, non-energy intensive conditions. Briefly, a method of depolymerization comprises providing a reaction mixture comprising a transition metal catalyst, and a polymer or oligomer having a backbone including one or more cyclobutane units, and decomposing or depolymerizing the polymer or oligomer in the presence of the transition metal catalyst to provide diene monomer or alkene monomer, wherein the transition metal catalyst is of Formula (I):

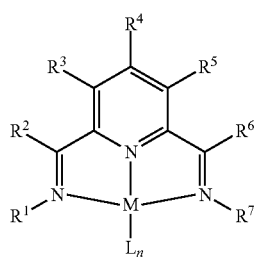

wherein M is selected from the group consisting of iron, cobalt and nickel and wherein $R^1$-$R^7$ are independently selected from the group consisting of hydrogen, alkyl, heteroalkyl, cycloalkyl, heterocycloalkyl, aryl and heteroaryl, wherein the alkyl, heteroalkyl, cycloalkyl, heterocycloalkyl, aryl and heteroaryl are optionally substituted with one or more substituents selected from the group consisting of ($C_1$-$C_{10}$)-alkyl, ($C_1$-$C_{10}$)-alkenyl, alkoxy, halo and hydroxyl; and wherein L is selected from the group consisting of halo, $N_2$, alkene/diene, carboxylate and CO; and n is 1 or 2.

In a further aspect, methods described herein further comprise reacting the diene monomer or alkene monomer to provide oligomers or polymers comprising the diene monomer and/or alkene monomer. In such embodiments, the oligomers or polymers are at least partially formed from the diene monomer and/or alkene monomer.

These and other embodiments are described further in the following detailed description.

DETAILED DESCRIPTION

Embodiments described herein can be understood more readily by reference to the following detailed description, examples and drawings and their previous and following descriptions. Elements, apparatus and methods described herein, however, are not limited to the specific embodiments presented in the detailed description, examples and drawings. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "from 5 to 10" or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

In one aspect, a method of depolymerization comprises providing a reaction mixture comprising a transition metal catalyst, and a polymer or oligomer having a backbone including cyclobutane units, and decomposing or depolymerizing the polymer or oligomer to provide diene monomer, wherein the transition metal catalyst is of Formula (I):

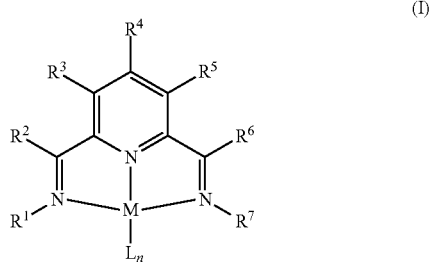

wherein M is selected from the group consisting of iron, cobalt and nickel and wherein $R^1$-$R^7$ are independently selected from the group consisting of hydrogen, alkyl, heteroalkyl, cycloalkyl, heterocycloalkyl, aryl and heteroaryl, wherein the alkyl, heteroalkyl, cycloalkyl, heterocycloalkyl, aryl and heteroaryl are optionally substituted with one or more substituents selected from the group consisting of ($C_1$-$C_{10}$)-alkyl, ($C_1$-$C_{10}$)-alkenyl, alkoxy, halo and hydroxyl; and wherein L is selected from the group consisting of halo, $N_2$, alkene/diene, carboxylate and CO; and n is 1 or 2. The transition metal catalyst can be present in the reaction mixture in any desired amount consistent with the technical objectives described herein. In some embodiments, the transition metal catalyst is present in the reaction mixture in an amount of 1-10 mol. % or 2-5 mol. %.

Figure 2A:
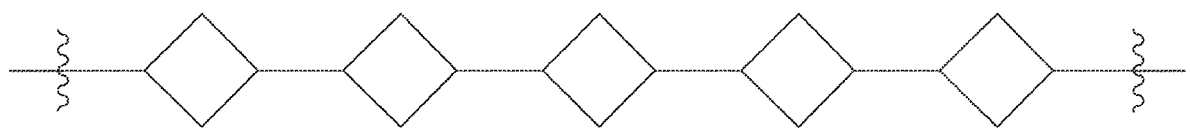
FIG. 2A illustrates a polymer comprising cyclobutane units according to some embodiments.
Figure 2B:
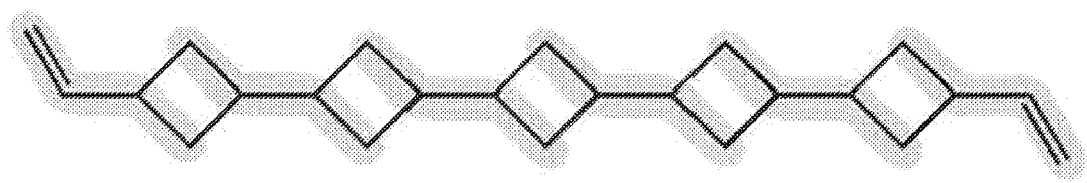
FIG. 2B illustrates incorporation of atoms from adjacent diene monomers into a cyclobutane unit according to some embodiments.

Turning now to specific components, the polymer or oligomer of the reaction mixture comprises cyclobutane units in the polymer or oligomer backbone. In forming part of the backbone, the cyclobutane units are not pendant groups. FIG. 2A illustrates a polymer comprising cyclobutane units in the polymer backbone according to some embodiments. In the embodiment of FIG. 2A, the cyclobutane units exhibit a 1,3-incorporation into the polymer backbone. Moreover, the cyclobutane units are directly linked with one another. In other embodiments, the linked cyclobutane units can exhibit a 1,2-incorporation into the polymeric backbone. A mixture of 1,3-incorporation and 1,2-incorporation of cyclobutane units is also possible. Cyclobutane units of the polymer, for example, incorporate atoms from linked butadiene monomers, as illustrated in FIG. 2B.

Figure 3:
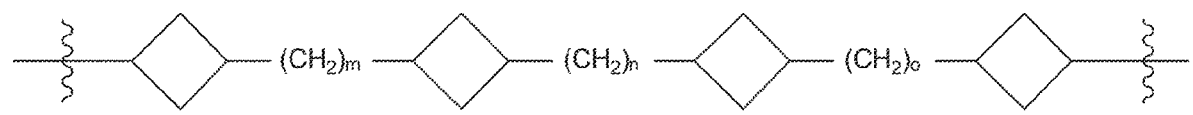
FIG. 3 illustrates a polymer comprising cyclobutane units according to some embodiments.

FIG. 3 illustrates another embodiment of a polymer comprising cyclobutane units in the polymer backbone. In the embodiment of FIG. 3, the cyclobutane units are separated by one or more methylene groups. Depending on identity of the diene monomer component, m, n and p can be the same or can vary from one another. m, n and p can independently have any value. In some embodiments, for example, m, n and p are independently selected from 0-10. Additionally, the cyclobutane units may be separated by one or more heteroatoms or heteroatom moieties (O, NR, $SiR_2$, etc.). In further embodiments, the cyclobutane units may be separated by one more ring structures, such as cycloalkyl or heterocycloalkyl. Any combination of methylene groups, heteroatoms and/or ring structures may also separate the cyclobutane units.

Polymeric species comprising cyclobutane units in the polymer backbone may also exhibit tacticity. Depending on specific identity of the diene monomer component, the polymer can be isotactic, syndiotactic or atactic. In some embodiments, polymeric species described herein can also comprise one or more pendent groups. Pendent groups, for example, can comprise alkyl or alkenyl moieties. Substituted diene monomer can be employed to incorporate pendant groups into the polymer. In some embodiments, isoprene or 2-vinyl-1,3-butadiene monomer can result in polymer comprising alkyl and alkenyl pendant groups, respectively. The pendent groups can provide additional functionality for cross-linking or altering chain packing and/or crystallinity. In some embodiments, polymers described herein are entirely aliphatic.

Chain ends of polymeric or oligomeric species described herein can exhibit reactive moieties or functionalities permitting incorporation of the polymer into various architectures including, but not limited to, block copolymers, graft copolymers and/or crosslinked structures. In some embodiments, for example, the chain end can comprise one or more functionalities having one or more points of unsaturation, including vinyl or alloy moieties. In other embodiments, chain ends can comprise a capping agent. The capping agent may provide orthogonal protection for reaction specificity and/or self-assembled architectures comprising the polymer. Capping agents can also be chemical modified to impart various functionalities including hydroxyl, amine, carboxyl or glycol moieties. In some embodiments, capping agents are coupled to one or more polymer ends via hydrofunctionalization including, but not limited to, hydroboration, hydrosilylation and hydroformylation.

Notably, oligomers can have any of the foregoing properties described herein for polymeric species. Oligomers can have any desired chain length. In some embodiments, for example, an oligomer incorporates as few as 2 cyclobutane units. Oligomer, in some embodiments, can have 2-5 or 2-10 cyclobutane units.

As described herein, the polymer or oligomer is decomposed in the presence of the transition metal catalyst to provide diene monomer or alkene monomer. The resulting diene monomer can comprise conjugated diene such as 1,3-butadiene and/or substituted 1,3-butadiene. Alternatively, the diene monomer component can comprise non-conjugated diene or a mixture of conjugated diene and non-conjugated diene. Specific composition of the diene monomer is dependent on the structure and properties of the polymer or oligomer being decomposed. Alkene monomer, some embodiments, comprises ethylene monomer. Specific compositions of the alkene monomer is dependent on the structure and properties of the polymer or oligomer being decomposed.

In some embodiments, at least 1 percent of diene monomer or alkene monomer is recovered from decomposition of the polymer or oligomer. In some embodiments at least 50-99 percent of diene monomer or alkene monomer is recovered from decomposition of the polymer or oligomer.

In some embodiments, the transition metal complex of Formula (I) can be provided to the reaction mixture under an inert atmosphere due to air and/or moisture sensitivity of the complex. The transition metal complex may also be formed in situ. Bench stable precursor, such as $MX_2$ (M=Fe, Co or Ni and X=halo, pseudohalide, sulfonate, etc.) can be added to the reaction mixture along with PDI [bis(imino)pyridine] ligand and reductant (RMgX, RLi, $NaBHEt_3$, Mg, $AlR_3$, etc.) to generate the transition metal complex in situ. The transition metal complex of Formula (I) can be present in the reaction mixture in any amount consistent with the technical objectives described herein.

The reaction mixture is heated to temperatures suitable for conducting the depolymerization reaction. In some embodiments, the reaction mixture is heated to a temperature less than 55° C. The reaction mixture, for example, can be heated to a temperature of 45-50° C. Moreover, the reaction mixture can be placed under static vacuum with stirring during the depolymerization reaction. The depolymerization reaction conditions described herein mark a substantial departure from prior, energy intensive depolymerization methods, including high temperature pyrolytic methods.

Diene monomer and/or alkene monomer can be separated and collected from the depolymerization reaction mixture by any suitable separation technique. In some embodiments, for example, molecular sieves can be employed for the separation of diene monomer and/or alkene monomer. Moreover, separation or collection of diene monomer and/or alkene monomer can occur during the depolymerization reaction. Alternatively, separation or collection of the diene monomer and/or alkenre monomer can occur after the depolymerization reaction.

In a further aspect, methods described herein further comprise reacting the diene monomer or alkene monomer to provide oligomers or polymers comprising the diene monomer and/or alkene monomer. In some embodiments, for example, the diene monomer is reacted to form homopolymer. Alternatively, the diene monomer can be reacted with one or more other monomeric species to provide various copolymers. In some embodiments, polymerization of diene monomer can take place in the presence of transition metal complex of Formula (I) described herein. In some embodiments, polymerization of diene monomer can be administered according to the disclosure of U.S. patent application Ser. No. 16/239,938 which is incorporated herein by reference in its entirety. Therefore efficiencies can be realized by employing the same or substantially similar transition metal complexes for both polymerization and depolymerization of cyclobutane polymers and/or oligomers.

These and other embodiments are further illustrated by the following non-limiting examples.

Figure 1:
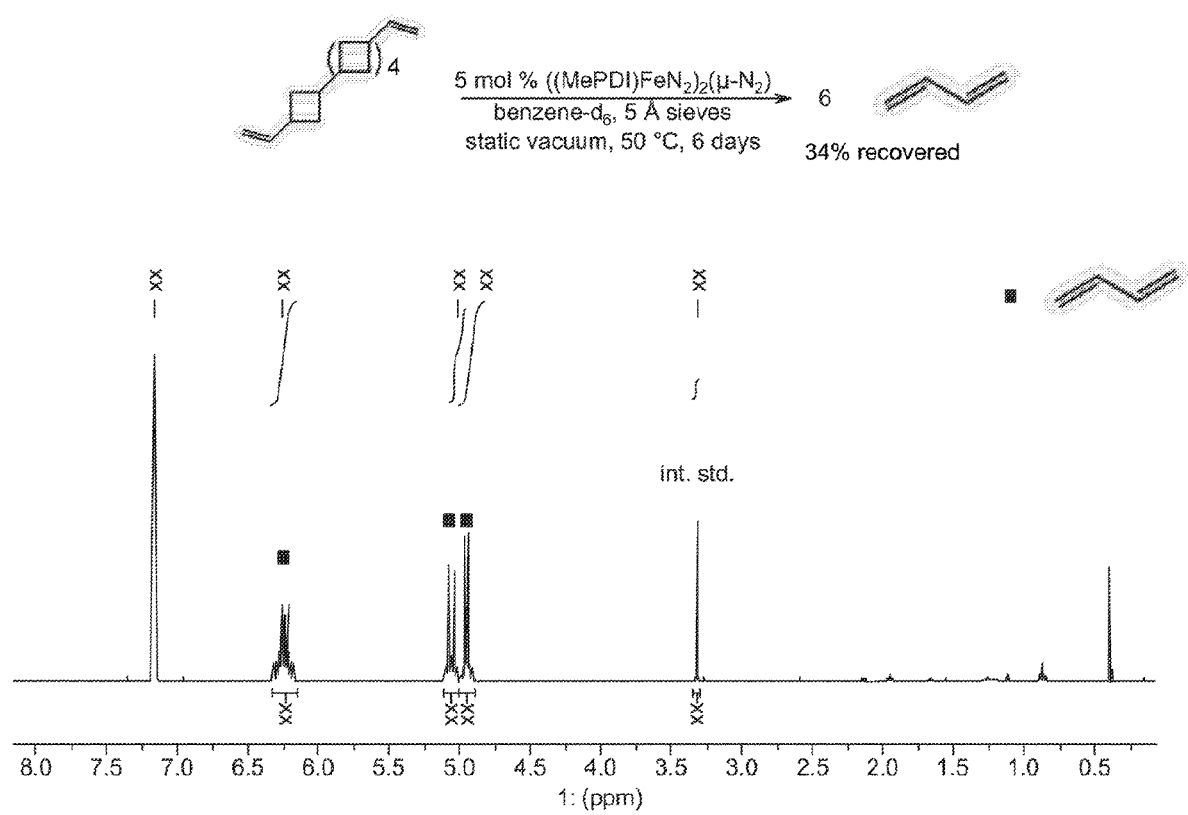
FIG. 1 is an $^1$H NMR spectrum of the volatile products including diene monomer formed from the catalytic decomposition of (1,n'-divinyl)polycyclobutane, according to some embodiments.

Example 1—Polymer Depolymerization (1,n'-divinyl)polycyclobutane was depolymerized according to the reaction scheme in FIG. 1 to recover 1,3-butadiene monomer. FIG. 1 provides a $^1$H NMR spectrum of the products from the catalytic depolymerization. The diene monomer was subsequently separated from the transition metal complex and molecular sieves by vacuum distillation.

Figure 6:
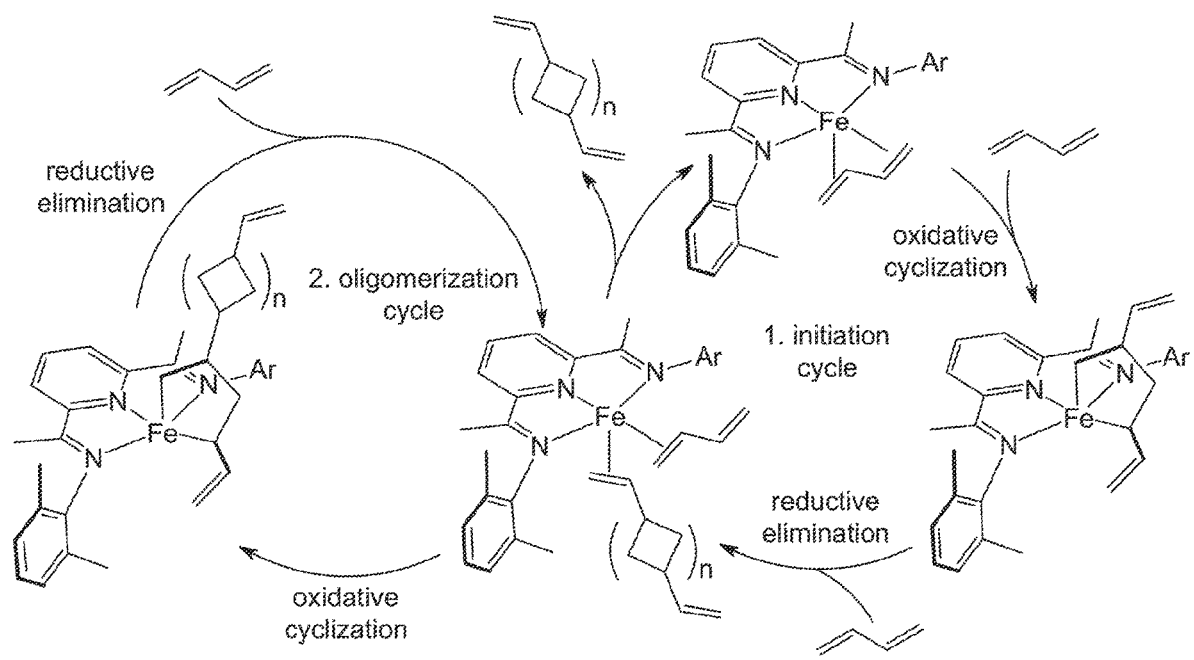
FIG. 6 illustrates a proposed catalytic cycle which depicts [2+2]-cyclodimerization of butadiene in the initiation cycle (left) generates 1,3-divinylcyclobutane, which then proceeds as an olefin in the oligomerization cycle (right).

In general, to 50-ml thick-walled glass vessel in the glove box was added a stir bar and 8 mg of 5-Å molecular sieves, then 0.0264 mmol of substrate in 700 μl of benzene-d6 was added to the vessel using a syringe. A stock solution containing 5 mg (0.0066 mmol) of $((^{Me}PDI)FeN_2)_2(\mu-N_2)$ in 400 μl of benzene-d6 was freshly prepared, of which 99 μl (0.00132 mmol, 0.05 equiv.) was added to the reaction vessel. The vessel was immediately sealed, frozen in liquid nitrogen and evacuated on a high-vacuum line. The flask was thawed, added to an oil bath at 50° C. and stirred vigorously for six days. After this time, all volatile contents of the reaction flask were vacuum-transferred to a J Young tube containing 50-150 μl of a 0.0416 M solution of 1,3,5-trimethoxybenzene in benzene-d6, and the volatiles were analysed by $^1$H NMR. Yields of butadiene and ethylene are reported relative to the 1,3,5-trimethoxybenzene internal standard, using the peak appearing at 4.93 ppm for quantification of butadiene Example 2—Mechanistic Studies Studies on the mechanism of [2+2] cycloadditions of olefins and dienes and DFT/TST calculations, were used to develop a unified catalytic cycle for the generation of oligomeric materials as presented in FIG. 6. Examination of the reaction landscape with three different functionals revealed a sequence of transformations in which an oxidative cyclization event occurs from a putative iron bis(diene) intermediate. Oxidative cyclization produces a divinylated metallacycle from which C—C bond-forming reductive elimination occurs to generate the cyclobutane ring. One of the vinyl groups of the formed 1,3-divinylcyclobutane then proceeds as a substrate in another oxidative cyclization event. Propagation by sequences of oxidative cyclization, reductive elimination and engagement of another vinyl group of the oligocyclobutane result in propagation of the cyclobutyl repeat units along the chain.

Figure 7:
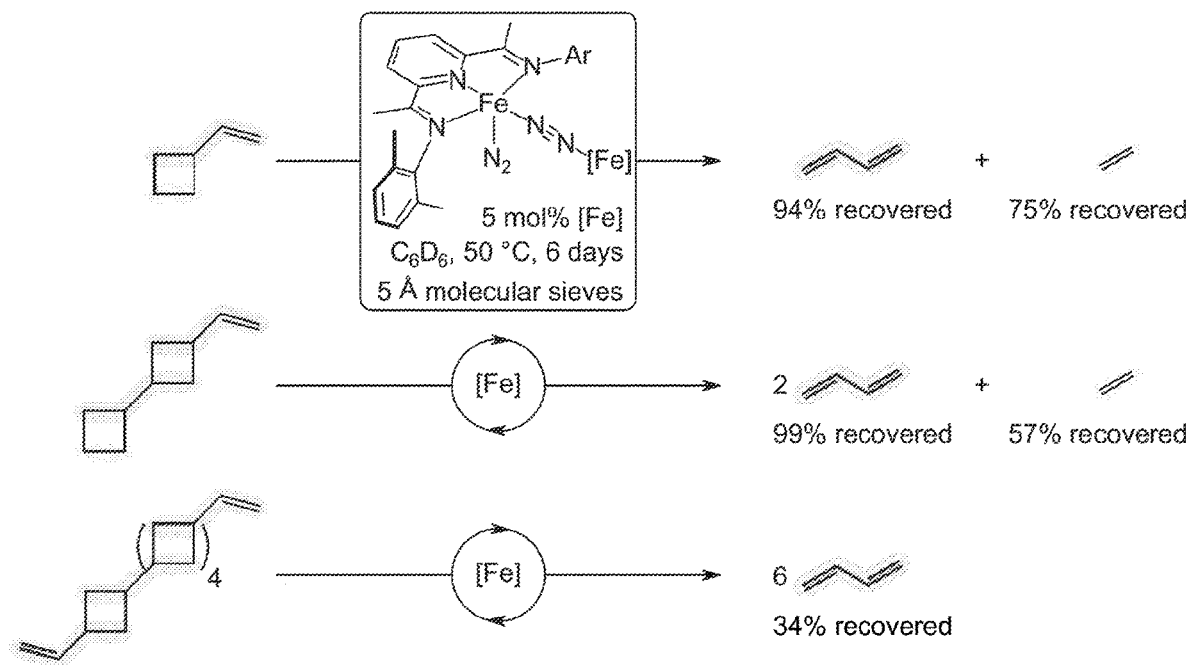
FIG. 7 illustrates catalytic chemical recycling of example cyclobutane structures. The top reaction depicts an example of quantitative decomposition of vinylcyclobutane affording 1 equiv. of butadiene and 1 equiv. of ethylene. The middle reaction depicts an example of quantitative decomposition of 3-vinyl-1,1'-bicyclobutane affording 2 equiv. of butadiene and 1 equiv. of ethylene. The bottom reaction depicts an example of the partial deoligomerization of (1,5'-divinyl)polycyclobutane with butadiene as the sole recovered monomer.

Exploration of the oligomerization sequence across three different solvent models at the TPSSh/RKS/LACV3P+//LACVP level of theory also indicates that the overall reaction is close to thermoneutral. In this energy landscape analysis, substantial overestimation of entropic contributions excludes the use of free-energy differences (ΔG); as such, energy differences were calculated using only the self-consistent field energy (SCFE) plus the ZPE35. Comparison of the energy of the growing oligomer chain (INT4) and the monomer coordinated (MePDI)Fe precatalyst (R) shows that both species are within 2±1.2 kcal mol$^{-1}$, supporting an overall near thermoneutral process. This is corroborated by the energy difference between the growing oligomer and butadiene, which is, −7.2±1.6 and 6.2±1.6 kcal mol$^{-1}$ for Δ(E+ZPE) and ΔG, respectively. The former energy difference excludes entropy and internal energy contributions, which are problematic within the rigid-rotor harmonic approximation. As such, the true energy difference will be higher. The computational data also help to corroborate the NMR data identifying alternate dispositions of cyclobutyl rings within the oligomer, as the calculations for each cyclobutyl disposition show that the stereochemical probabilities for the first turnover are equal for initial generation of a syn or anti cyclobutane, while subsequent turnovers prefer opposite configurations. DFT/TST calculations further established C—C bond-forming reductive elimination as the turnover-limiting step. A key motivator for pursuing the [2+2]-cycloaddition/oligomerization strategy was the potential for reversibility and chemical recycling—a prospect seemingly accessible given the calculated thermodynamics of the overall reaction. Although ring-opening C—C oxidative addition of vinylcyclobutane with (($^{Me}$PDI)FeN$_2$)$_2$(µ–N$_2$) and cycloreversion had been demonstrated previously in stoichiometric experiments, the viability of this reverse reaction under catalytic conditions had yet to be demonstrated. The catalytic decomposition of such structures was posited to be potentially challenging given the strong energetic preference for coordination of butadiene to the iron catalyst. Control experiments indicated that sequestration of the butadiene formed upon retro-cycloaddition was key to achieving meaningful levels of deoligomerization. As such, activated 5-Å molecular sieves were added to a benzene-d$_6$ solution containing (($^{Me}$PDI) FeN$_2$)$_2$(µ–N$_2$) and vinylcyclobutane to sequester any liberated butadiene. After six days at 50° C., re-isolation of the adsorbed volatiles from the sieves and $^1$H NMR analysis established 99% consumption of the vinylcyclobutane and recovery of the constituent ethylene (75% yield) and butadiene (94% yield; FIG. 7 (top)). Similarly, catalytic retro-[2+2]-cycloaddition of 3-vinyl-1,1'-dicyclobutane, isolated from the [2+2]-cycloaddition/oligomerization of ethylene and butadiene was reverted to the starting hydrocarbons. Under the same conditions, the deoligomerization of 3-vinyl-1,1'-dicyclobutane regenerated 57% of total ethylene and 99% of total butadiene (FIG. 7 (middle)).

Extension to catalytic chemical recycling of (1,n'-divinyl) oligocyclobutane was demonstrated on the organic soluble material with a number-average length of five cyclobutyl rings (Mn=324 g mol–1), obtained from an oligomerization reaction run for 24 h. In benzene-d6 solution under static vacuum, 34% of butadiene was recovered after heating at 50° C. for six days (FIG. 7 (bottom)). The success of the deoligomerization was dependent on the volume of reaction vessel used, probably a result of product inhibition of butadiene on the activity of the catalyst. Indeed, examination of a catalytic deoligomerization by 1H NMR spectroscopy indicated that butadiene coordination to the iron catalyst inhibits the retro-cycloaddition process. Extensions to the deoligomerization of an oligomer consisting of an average of 10 enchained cyclobutane rings using the above conditions resulted in 5% recovery of butadiene monomer. Cross-linking of the oligomer chains does not appear responsible for the low recovery of monomer, as a gelation test indicated only minimal amounts (~2% by weight) of insoluble residue are present in bulk material. More plausibly limitations in experimental setup likely contribute to the relatively low amount of recovered monomer; furthermore, solubilizing the higher-molecular-weight oligomer must be balanced with the temperatures at which the catalyst can operate without decomposing in solution. Current efforts are devoted to more sophisticated engineering to improve recovery. Nevertheless, the ability to recover pristine butadiene clearly establishes this hydrocarbon oligomer is amenable to chemical recycling using the same catalyst used for its synthesis.

Example 3—Polymer Preparation

Preparation of (1,n'-divinyl)oligocyclobutane. A 50-ml thick-walled glass vessel containing a stir bar was charged with 12 mg (0.0125 mmol) of (($^{Me}$PDI)FeN$_2$)$_2$(µ–N$_2$) in a nitrogen-filled glovebox. The flask was sealed, brought out of the glove box and degassed on a high-vacuum line. Butadiene (12.5 mmol) was added to the reaction vessel using a calibrated gas bulb. The flask was sealed, warmed to room temperature, then added to an oil bath at 50° C. for 72 h. Complete consumption of liquid butadiene and deposition of a white solid on the walls of the flask was observed. After 72 h, the reaction was quenched by vacuum transferring the volatiles into a flask containing 800-1,000 µl of chloroform-d for analysis by 1H NMR, in which only residual butadiene was observed. The nonvolatiles were extracted with ~10 ml of ethyl acetate, producing a light tan solution and off-white precipitate. The ethyl acetate soluble fraction was decanted away from the insoluble material and passed through a pipette plug containing ~3 cm of silica, eluting with additional ethyl acetate. Both fractions were evaporated to dryness. The ethyl acetate soluble material was washed with ~5 ml of methanol and dried under vacuum to yield 0.043 g (7% yield based on starting butadiene consumed) of (1,n'-divinyl)oligocyclobutane (Mn≈486 g mol–1, eight total cyclobutyls) as a white semisolid. Additionally, 0.299 g (47% yield based on starting butadiene consumed) of ethyl acetate insoluble (1,n'-divinyl)oligocyclobutane (Mn≈973 g mol–1, 17 total cyclobutyls) was isolated as a light tan crystalline powder.

For analysis of the ethyl acetate insoluble material by NMR, ~3 ml of o,o-dichlorobenzene was added to ~25 mg of the light tan powder. The heterogeneous mixture was heated with stirring to 120° C. in a vial, and dissolution of the solid was observed. The hot solution was added dropwise into a vial containing 5 ml of vigorously stirring methanol at ambient temperature. The resultant white precipitate was isolated by vacuum filtration and suspended in 600 µl of 1,1,2,2-tetrachloroethane-d2. The suspension was heated with stirring to 120° C., after which the contents were transferred to an NMR tube and analysed by 1H and 13C NMR at a probe temperature of 120° C.

Preparation of (1,n'-diethyl)oligocyclobutane. A glass-lined autoclave (600 ml) equipped with a polytetrafluoroethylene-coated magnetic stir bar was charged with (1,n'-divinyl)oligocyclobutane (M$_n$≈581 g mol–1, ~10 cyclobutyls, 1.00 g), cyclohexane (100 ml) and PtO$_2$ (0.01 g, 2.5 mol %). The autoclave was sealed and pressurized with H$_2$ (100 PSIG). It was then heated to 100° C. where it was allowed to react for 20 h. The reactor was cooled to ~80° C., where it was vented and opened. The reaction mixture, a homogenous, pale, yellow solution, was filtered hot to remove PtO$_2$. The filtrate was then concentrated to a solid under reduced pressure to afford (1,n'-diethyl)oligocyclobutane as a colorless powder (yield: 0.75 g, 75%). The material was characterized by $^1$H and $^{13}$C{$^1$H} NMR (TCE-d2; 120° C.) spectroscopy and ATR spectroscopy to confirm consumption of vinyl groups.

Preparation of 3-vinyl-1,1'-dicyclobutane. A 200-ml thick-walled glass vessel containing a stir bar was charged with 93 mg (0.2 mmol) of (($^{Me}$PDI)FeN$_2$)$_2$(µ–N$_2$) in a nitrogen-filled glove box. The flask was sealed, brought out of the glove box, and degassed on a high-vacuum line. Butadiene (20 mmol) was added to the reaction vessel using a calibrated gas bulb. Without thawing the flask, ethylene (20 mmol) was added to the reaction vessel using a calibrated gas bulb. The flask was then thawed and stirred at ambient temperature for 48 h. Deposition of a liquid on the bottom of the flask was observed. After 48 h, the volatiles were vacuum-transferred at ambient temperature into another flask. Analysis of this material by 1H NMR indicated the formation of vinylcyclobutane (1.00 g, 61% isolated yield), consistent with a previous literature report. 3-Vinyl-1,1'-dicyclobutane was isolated from the remaining residue by vacuum transfer while gently heating the bulk material with a heat gun, and was obtained in 15% isolated yield (0.400 mg).

Example 4—Results

Figure 4:
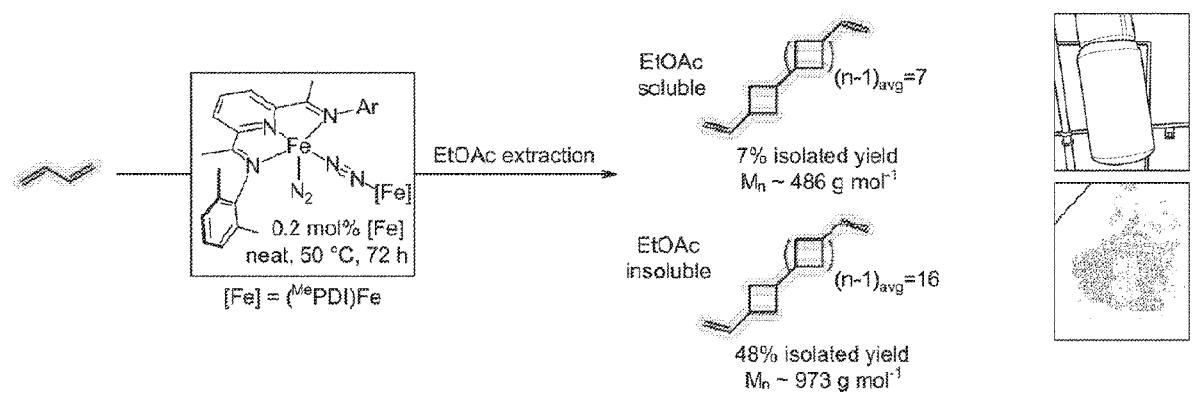
FIG. 4 illustrates oligomerization of butadiene under elevated temperatures and neat conditions produces lower-molecular-weight organic soluble (1,n'-divinyl)polycyclobutane and higher-molecular-weight insoluble (1,n'-divinyl)polycyclobutane.

Synthesis and characterization of the oligocyclobutane microstructure. Mechanistic studies support metallacyclic intermediates arising from oxidative cyclization of the unsaturated hydrocarbon substrates, often giving rise to cyclobutanes with high regio- and stereoselectivities. For diene-alkene [2+2] cycloaddition, the iron catalyst engages with only one of the alkenes of the diene, suggesting that a cascade cycloaddition oligomerization of 1,3-butadiene to yield a new microstructure of oligobutadiene. Dissolving the iron dinitrogen precatalyst $((^{Me}PDI)FeN_2)_2(\mu-N_2)$ $(^{Me}PDI=2,6-(2,6-Me-C_6H_3—N=CMe)2C_5H_3N)$ in neat butadiene resulted in consumption of the liquid monomer after three days at 50° C. and generated a white solid. Removal of the volatiles and extraction of the residue with ethyl acetate yielded a soluble, semisolid fraction and an insoluble, hard, crystalline, light tan powder (FIG. 4).

Characterization of the organic soluble fraction by one-dimensional (1D) and 2D NMR spectroscopies established that the oligomer microstructure was distinct from that of known polymers resulting from 1,4- or 1,2-addition of butadiene. Instead, the spectroscopic data established an oligomer of 1,3-linked cyclobutanes terminated by vinyl groups on both chain ends. NMR spectroscopic analysis of the crystalline fraction in 1,1,2,2-tetrachloroethane-d2 at 120° C. revealed analogous features, differing only in the increased ratio of repeat units to chain ends. Density functional theory (DFT) simulation of the NMR chemical shifts corroborated a 1,3-linked cyclobutane polymer structure. Quantitation of oligomer molecular weight, based on 1H NMR integrations, revealed that the organic soluble material has a number-averaged molecular mass (Mn) of 486 g mol–1, corresponding to an average of eight cyclobutyl repeat units, while the insoluble material has an Mn of 973 g mol–1, or a number-average chain of 17 cyclobutyl rings. Although both of these molecular weights were too low to be analyzed by gel permeation chromatography (GPC), the mass values obtained by 1H NMR spectroscopy were corroborated by mass spectrometry (atmospheric pressure chemical ionization (APCI) MS). On a multigram scale, molecular weights approximating 580 g mol$^{-1}$, or 10 enchained cyclobutanes, were routinely obtained. Deviation from the above reaction conditions through modification of the reaction temperature resulted in reduced-molecular-weight oligomers, while introduction of cyclohexane solvent in the reaction mixture ceased oligomerization altogether.

The iron-catalysed [2+2] oligomerization of butadiene was also initiated in the presence of ethylene. Adding equimolar amounts of ethylene and 1,3-butadiene to a vessel containing $((^{Me}PDI)FeN_2)_2(\mu-N_2)$ at ambient temperature over two days yielded vinylcyclobutane, as previously reported, along with oligomeric products arising from further [2+2] cycloaddition/oligomerization of the formed vinylcyclobutane with butadiene. The resulting oligomers consisted of cyclobutane repeat units terminated by a vinyl group on only one end on the chain. This result indicates that tailored control of the chain-end component of the oligocyclobutane is possible through choice of olefin coupling partner, representing a marked deviation from previous reports of 1,3-linked polycyclobutane structures.

The unique structure of the oligocyclobutanes prompted more detailed characterization studies. Although the products of butadiene [2+2]-cycloaddition/oligomerization are intrinsically achiral (meso), each cyclobutane repeat unit may be constituted with 1,3-substituents in either a syn or anti disposition. High-field NMR spectroscopy enabled the assignment and quantification of chain-end diad sequences and polymer-chain triad sequences. The results of comprehensive, quantitative NMR peak identification and integration yielded the following statistics on sequence distribution. First, there are equal amounts of syn and anti cyclobutane rings, and the same is true at the vinyl chain ends. Second, adjacent cyclobutane rings have a higher probability (~60%) of having the opposite disposition (that is, anti-syn or syn-anti). Density functional and transition state theory (DFT/TST) calculations for [2+2]-cycloaddition of butadiene by [(MePDI)Fe] agree with the NMR analysis; namely, the vinyl-chain-end cyclobutane has equal probability of being anti or syn $(\Delta\Delta(E+ZPE)\ddagger<1$ kcal mol–1 for reductive elimination (ZPE, zero point energy); and subsequent [2+2]-cycloadditions favour the opposite disposition $(\Delta\Delta(E+ZPE)\_$ TPSSh$\ddagger\approx2$ kcal mol–1 for reductive elimination.

Although other pyridine(diimine) iron precatalysts were also competent for the [2+2]-cycloaddition oligomerization, they afforded oligomers of similar or lower molecular weight and no perturbation of the previously observed tacticity. Notably, in situ activation of a pyridine(diimine) iron dihalide precatalyst with magnesium butadiene generated oligocyclobutane of slightly lower molecular weight (~865 g mol–1). Linear 1,4-products were also formed and probably arise from incomplete reduction of the iron dihalide precatalyst or other side reactions generating unidentified iron compounds that promote unwanted acyclic material. Although the search for other complexes that are able to catalyse this transformation are ongoing, a related redox-active pyridine(dicarbene) iron dinitrogen compound as well as a phosphine-ligated cobalt complex known to catalyse [2+2] transformations of olefins produced no cyclic oligomer.

Figure 5A:
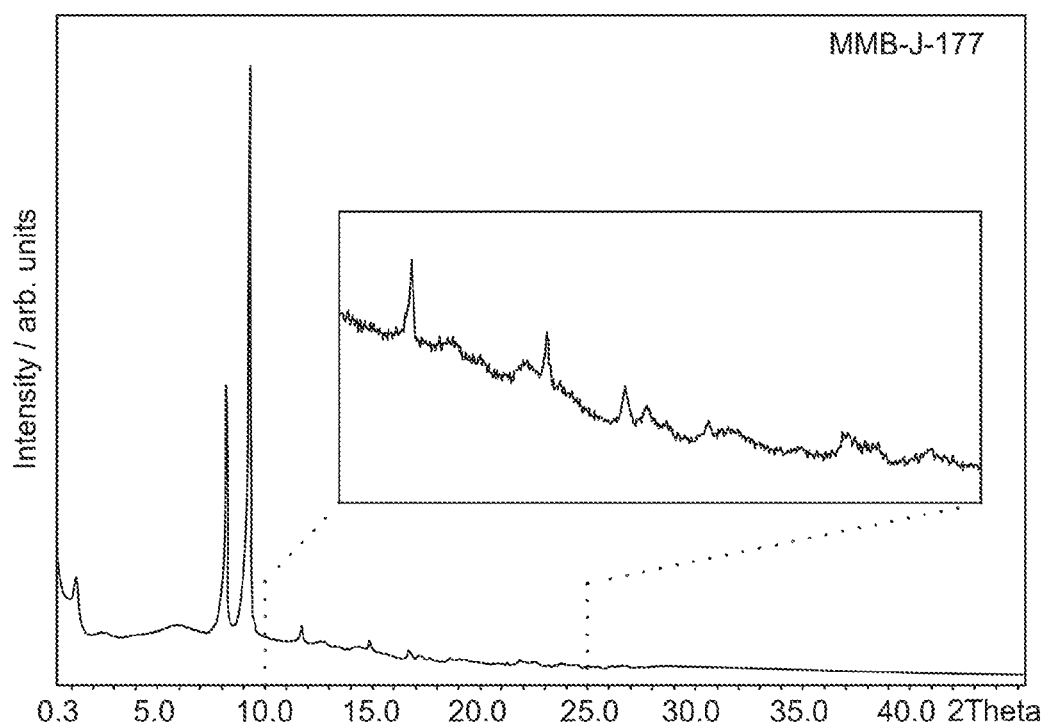
FIG. 5A illustrates a graph displaying VT-WAXS data indicating amorphous material crystallizing upon cooling.

Crystallographic and thermal properties of oligocyclobutanes. The crystallinity of the insoluble fraction obtained from butadiene homo-oligomerization catalysed by $((^{Me}PDI)FeN_2)_2(\mu-N_2)$ was confirmed by wide-angle X-ray scattering (WAXS) studies. Although unambiguous structural determination was precluded by the inability to obtain a crystal suitable for single-crystal X-ray diffraction, comparison of the powder pattern to that of known hydrocarbon polymers bore no analogy, confirming a unique crystalline microstructure. Variable-temperature (VT) WAXS revealed that the oligomer regained crystallinity upon cooling from 170° C. to 30° C. (FIG. 5A), with a rotator phase appearing at a temperature range of 110-130° C. Taken together, these data suggest a temperature-dependent ordering of domains within the oligocyclobutane structure.

Thermal data obtained on the crystalline oligomer provide insights into the robustness of this new microstructure. Thermal gravimetric analysis (TGA) of the crystalline material revealed a bulk decomposition event at an onset temperature of 413° C. Analysis of the volatile decomposition products by TGA-gas chromatography/mass spectrometry (TGA-GC/MS) indicated that butadiene is not evolved during bulk decomposition; thus, retro-cycloaddition is not thermally induced. The overall thermal properties of the material parallels that of 1,4-polybutadiene of approximately the same Mn, despite the drastically different morphologies of the materials. Differential scanning calorimetry (DSC) indicated that the crystalline domains of the cyclobutyl oligomer are recoverable upon heating from –80° C. to 250° C. and subsequently cycling from 250° C. to 30°

Figure 5B:
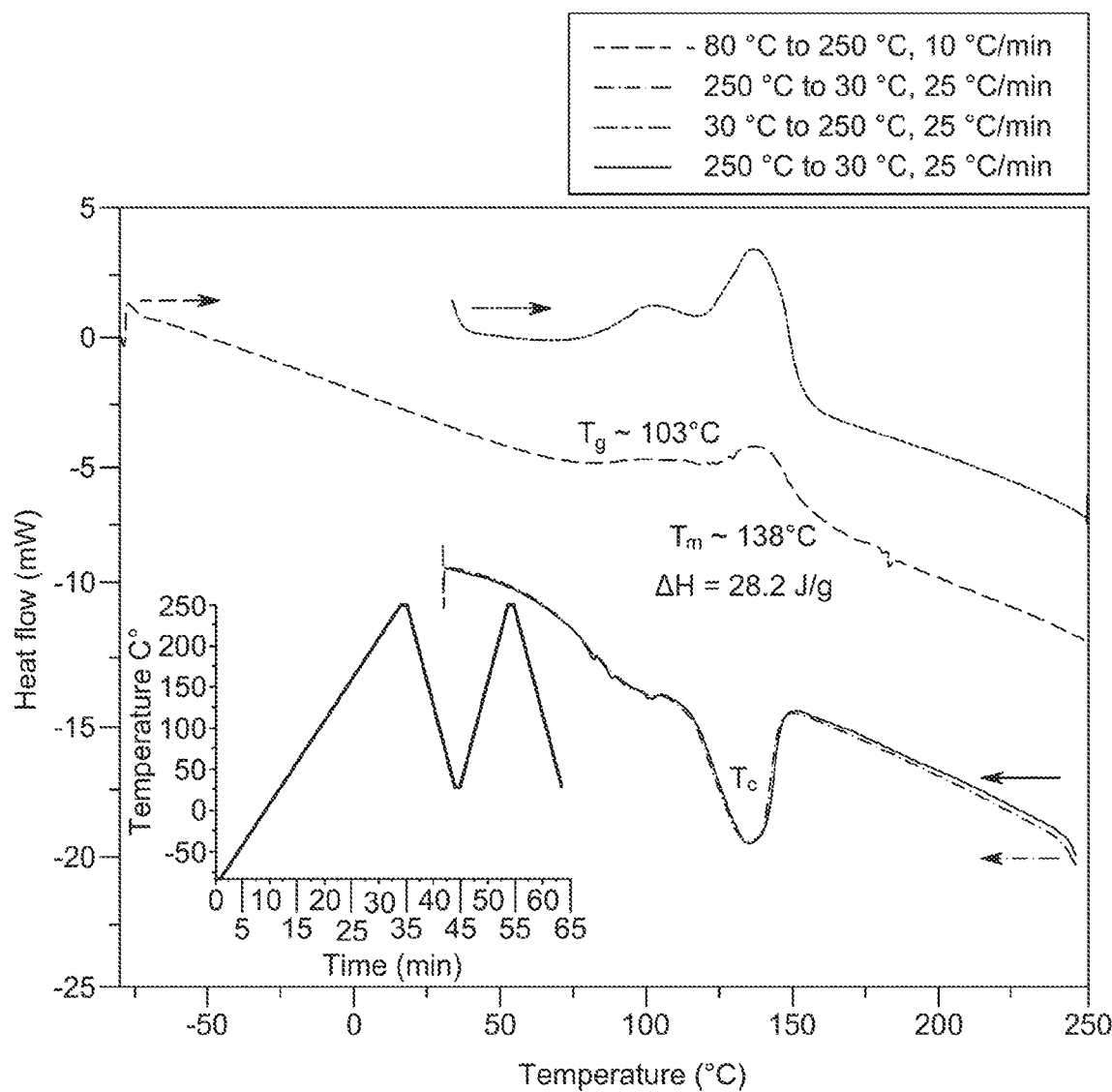
FIG. 5B illustrates a graph displaying DSC data demonstrating retention of melting and crystallization temperatures upon temperature cycling. Isothermal regions have been omitted for clarity.

C. twice (FIG. 5B). The bimodal melting temperatures are ascribed to an initial transition of the crystalline domain to a rotator phase (onset at ~110° C.), with subsequent transition to completely amorphous material (onset at 135° C.), corroborating the VT-WAXS features. The melting event at 155° C. is analogous to the reported melting temperature of the 90% trans 1,4-polybutadiene congener33. Additional DSC analysis at variable scan rates revealed a thermal event at approximately −10° C., consistent with a glass transition.

To assess the impact of vinyl end groups on thermal properties, a representative oligomer was hydrogenated to (1,n'-diethyl) oligocyclobutane and its thermal properties were examined. By DSC, only small (~5° C.) shifts in the thermal events were observed, but the major features between the unsaturated and saturated variants remained unchanged. Oxidation induction time testing of both the hydrogenated and native material indicated that both oligomers undergo rapid oxidation (≤10 min), with the hydrogenated material being slightly more resistant to oxidation at 200° C.

Simulation of a crystal lattice representative of the observed scattering data was pursued computationally using molecular dynamics (MD) simulations. Multiple (1-n'-divinyl)cyclobutane oligomers (n=17) were generated with sequence distributions (syn/anti diads) consistent with those observed by NMR spectroscopy. Low-energy conformers obtained from the molecular mechanics simulations were used as inputs to simulate crystalline polymorphs from which a series of low-energy P21 symmetric unit cells were obtained. The resulting strand is comprised primarily of alternating syn and anti dispositions of cyclobutyl rings, consistent with the NMR and computational data. MD simulations were also used to generate an amorphous supercell generating a simulated scattering pattern consistent with experimental data obtained at 170° C.

Chemical recycling of cyclobutane motifs. Based on studies on the mechanism of [2+2] cycloadditions of olefins and dienes and DFT/TST calculations, a unified catalytic cycle for the generation of oligomeric materials is presented in FIG. 6. Examination of the reaction landscape with three different functionals revealed a sequence of transformations in which an oxidative cyclization event occurs from a putative iron bis(diene) intermediate. Oxidative cyclization produces a divinylated metallacycle from which C—C bond-forming reductive elimination occurs to generate the cyclobutane ring. One of the vinyl groups of the formed 1,3-divinylcyclobutane then proceeds as a substrate in another oxidative cyclization event. Propagation by sequences of oxidative cyclization, reductive elimination and engagement of another vinyl group of the oligocyclobutane result in propagation of the cyclobutyl repeat units along the chain.

Exploration of the oligomerization sequence across three different solvent models at the TPSSh/RKS/LACV3P+// LACVP level of theory also indicates that the overall reaction is close to thermoneutral. In this energy landscape analysis, substantial overestimation of entropic contributions excludes the use of free-energy differences (ΔG); as such, energy differences were calculated using only the self-consistent field energy (SCFE) plus the ZPE35. Comparison of the energy of the growing oligomer chain and the monomer coordinated (MePDI)Fe precatalyst shows that both species are within 2±1.2 kcal mol$^{-1}$, supporting an overall near thermoneutral process. This is corroborated by the energy difference between the growing oligomer and butadiene, which is, −7.2±1.6 and 6.2±1.6 kcal mol$^{-1}$ for Δ(E+ZPE) and ΔG, respectively. The former energy difference excludes entropy and internal energy contributions, which are problematic within the rigid-rotor harmonic approximation. As such, the true energy difference will be higher. The computational data also corroborate the NMR data identifying alternate dispositions of cyclobutyl rings within the oligomer, as the calculations for each cyclobutyl disposition show that the stereochemical probabilities for the first turnover are equal for initial generation of a syn or anti cyclobutane, while subsequent turnovers prefer opposite configurations. DFT/TST calculations further established C—C bond-forming reductive elimination as the turnover-limiting step (FIG. 6), consistent with previous mechanistic studies on analogous intermolecular [2+2] reactions incorporating dienes.

A key motivator for pursuing the [2+2]-cycloaddition/oligomerization strategy was the potential for reversibility and chemical recycling—a prospect seemingly accessible given the calculated thermodynamics of the overall reaction. Although ring-opening C—C oxidative addition of vinylcyclobutane with (($^{Me}$PDI)FeN$_2$)$_2$(μ-N$_2$) and cycloreversion had been demonstrated previously in stoichiometric experiments, the viability of this reverse reaction under catalytic conditions had yet to be demonstrated. The catalytic decomposition of such structures was posited to be potentially challenging given the strong energetic preference for coordination of butadiene to the iron catalyst. Control experiments indicated that sequestration of the butadiene formed upon retro-cycloaddition may help to achieve meaningful levels of deoligomerization. As such, activated 5-Å molecular sieves were added to a benzene-d6 solution containing (($^{Me}$PDI)FeN$_2$)$_2$(μ-N$_2$) and vinylcyclobutane to sequester any liberated butadiene. After six days at 50° C., re-isolation of the adsorbed volatiles from the sieves and $^1$H NMR analysis established 99% consumption of the vinylcyclobutane and recovery of the constituent ethylene (75% yield) and butadiene (94% yield; FIG. 7 (top)). Similarly, catalytic retro-[2+2]-cycloaddition of 3-vinyl-1,1'-dicyclobutane, isolated from the [2+2]-cycloaddition/oligomerization of ethylene and butadiene, was reverted to the starting hydrocarbons. Under the same conditions, the deoligomerization of 3-vinyl-1,1'-dicyclobutane regenerated 57% of total ethylene and 99% of total butadiene (FIG. 7 (middle)).

Extension to catalytic chemical recycling of (1,n'-divinyl) oligocyclobutane was demonstrated on the organic soluble material with a number-average length of five cyclobutyl rings (Mn=324 g mol$^{-1}$), obtained from an oligomerization reaction run for 24 h. In benzene-d6 solution under static vacuum, 34% of butadiene was recovered after heating at 50° C. for six days (FIG. 7 (bottom)). The success of the deoligomerization was dependent on the volume of reaction vessel used, probably a result of product inhibition of butadiene on the activity of the catalyst. Indeed, examination of a catalytic deoligomerization by $^1$H NMR spectroscopy indicated that butadiene coordination to the iron catalyst inhibits the retro-cycloaddition process. Extensions to the deoligomerization of an oligomer consisting of an average of 10 enchained cyclobutane rings using the above conditions resulted in 5% recovery of butadiene monomer. Cross-linking of the oligomer chains does not appear responsible for the low recovery of monomer, as a gelation test indicated only minimal amounts (~2% by weight) of insoluble residue are present in bulk material. More plausibly limitations in experimental setup likely contribute to the relatively low amount of recovered monomer; furthermore, solubilizing the higher-molecular-weight oligomer must be balanced with the temperatures at which the catalyst can operate without decomposing in solution. Current efforts are devoted to more sophisticated engineering to improve recovery. Nevertheless, the ability to recover pristine butadiene clearly establishes this hydrocarbon oligomer is amenable to chemical recycling using the same catalyst used for its synthesis.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention

The invention claimed is:

1. A method of depolymerization comprising:
providing a reaction mixture comprising a transition metal catalyst, and a polymer or oligomer having a backbone including cyclobutane units; and
depolymerizing the polymer or oligomer to provide diene monomer or alkene monomer, wherein the transition metal catalyst is of Formula (I):

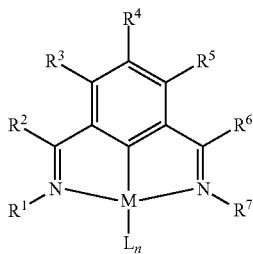

wherein M is selected from the group consisting of iron, cobalt and nickel and wherein $R^1$-$R^7$ are independently selected from the group consisting of hydrogen, alkyl, heteroalkyl, cycloalkyl, heterocycloalkyl, aryl and heteroaryl, wherein the alkyl, heteroalkyl, cycloalkyl, heterocycloalkyl, aryl and heteroaryl are optionally substituted with one or more substituents selected from the group consisting of $(C_1-C_{10})$-alkyl, $(C_1-C_{10})$-alkenyl, alkoxy, halo and hydroxyl; and wherein L is selected from the group consisting of halo, $N_2$, alkene/diene, carboxylate and CO; and n is 1 or 2.

2. The method of claim 1, wherein the diene monomer is conjugated.

3. The method of claim 1, wherein the diene monomer is non-conjugated.

4. The method of claim 1, wherein the diene monomer comprises a mixture of conjugated diene and non-conjugated diene.

5. The method of claim 2, wherein the diene monomer is 1,3-butadiene or substituted 1,3-butadiene.

6. The method of claim 1, wherein the alkene monomer is ethylene.

7. The method of claim 1, wherein the cyclobutane units comprise 1,2-cyclobutane.

8. The method of claim 1, wherein cyclobutane units comprise 1,3-cyclobutane.

9. The method of claim 1, wherein the cyclobutane units comprise a mixture of 1,2-cyclobutane and 1,3-cyclobutane.

10. The method of claim 1, wherein the cyclobutane units are separated by one or more methylenes in the polymer backbone.

11. The method of claim 1, wherein at least 1 weight percent diene monomer or alkene monomer is recovered from decomposition of the oligomer or the polymer.

12. The method of claim 1, wherein at least 50 percent diene monomer or alkene monomer is recovered from decomposition of the oligomer or the polymer.

13. The method of claim 1, wherein 90-99 percent diene monomer or alkene monomer is recovered from decomposition of the oligomer or the polymer.

14. The method of claim 1, wherein one or both chain ends of the polymer or oligomer are terminated with a functionality comprises an unsaturated moiety.

15. The method of claim 14, wherein the unsaturated moiety is a vinyl or ally moiety.

16. The method of claim 1, wherein diene monomer or alkene monomer is separated or collected from the reaction mixture.

17. The method of claim 16, wherein the diene monomer or alkene monomer is separated or collected from the reaction mixture during the depolymerization reaction.

18. The method of claim 16, wherein molecular sieves collect the diene monomer, alkene monomer or mixtures thereof.

19. The method of claim 1 further comprising reacting the diene monomer or alkene monomer to provide oligomers or polymers comprising the diene monomer or alkene monomer.

20. The method of claim 19, wherein the diene monomer or alkene monomer are reacted in the presence of the transition metal complex of Formula (I).

* * * * *